United States Patent [19]

Derlien

[11] Patent Number: 5,244,461
[45] Date of Patent: Sep. 14, 1993

[54] INFUSION PUMP WITH OCCLUSION SENSITIVE SHUTOFF

[75] Inventor: Michael L. Derlien, Watford, United Kingdom

[73] Assignee: Graseby Medical Limited, Cambridge, Great Britain

[21] Appl. No.: 743,392

[22] PCT Filed: Mar. 12, 1990

[86] PCT No.: PCT/GB90/00371
§ 371 Date: Aug. 14, 1991
§ 102(e) Date: Aug. 14, 1991

[87] PCT Pub. No.: WO90/10468
PCT Pub. Date: Sep. 20, 1990

[30] Foreign Application Priority Data
Mar. 10, 1989 [GB] United Kingdom ................. 8905494

[51] Int. Cl.[5] ..................... A61M 31/00; A61M 37/00
[52] U.S. Cl. .......................... 604/65; 604/66; 604/67; 604/154; 604/155; 128/DIG. 1; 128/DIG. 12
[58] Field of Search ................. 604/67, 131, 152, 154, 604/155, 191, 246, 207, 118, 65, 66, 121, DIG. 13; 128/DIG. 1, DIG. 12

[56] References Cited

U.S. PATENT DOCUMENTS

| 3,415,419 | 12/1968 | Jewett et al. | 604/155 |
|---|---|---|---|
| 3,425,416 | 2/1969 | Loughry | 604/155 |
| 3,456,649 | 7/1969 | Jewett | 604/155 |
| 3,858,581 | 1/1975 | Kamen | 128/DIG. 1 |
| 4,006,736 | 2/1977 | Kranys et al. | 128/DIG. 1 |
| 4,405,318 | 9/1983 | Whitney et al. | 128/DIG. 1 |
| 4,529,401 | 7/1985 | Leslie et al. | 128/DIG. 1 |
| 4,563,175 | 1/1986 | LaFond | 128/DIG. 12 |
| 4,620,848 | 11/1986 | Sutherland et al. | |
| 4,627,835 | 12/1986 | Fenton, Sr. | 128/DIG. 1 |
| 4,731,058 | 3/1988 | Doan | |
| 4,812,724 | 3/1989 | Langer et al. | |
| 4,952,205 | 8/1990 | Mauerer et al. | 604/246 |
| 5,034,004 | 7/1991 | Crankshaw | 128/DIG. 1 |

FOREIGN PATENT DOCUMENTS

| 1960788 | 1/1989 | Australia . |
|---|---|---|
| 4201985 | 1/1989 | Australia . |
| 0180453 | 5/1986 | European Pat. Off. ........... 604/67 |
| 0183400 | 6/1986 | European Pat. Off. . |
| 2724538 | 12/1978 | Fed. Rep. of Germany . |
| 2164566A | 3/1986 | United Kingdom . |

Primary Examiner—C. Fred Rosenbaum
Assistant Examiner—Mark Bockelman
Attorney, Agent, or Firm—Price, Heneveld, Cooper, DeWitt & Litton

[57] ABSTRACT

An infusion pump, suitable for medical applications, has a movable carriage which is arranged gradually to depress the plunger of a syringe. The carriage moves along a fixed rod at a rate determined by the rotation of a lead screw. Any excess pressure in the infusion line produces a back-pressure on the plunger which causes an axial force to be exerted on the carriage and thus on the lead screw. When this force exceeds a predetermined value, indicative of an occlusion of the infusion line, the lead screw will move axially so compressing a spring and causing a clutch to become decoupled, causing infusion to cease and an alarm to sound.

21 Claims, 1 Drawing Sheet

INFUSION PUMP WITH OCCLUSION SENSITIVE SHUTOFF

BACKGROUND OF THE INVENTION

The invention relates to infusion pumps adapted to receive a syringe containing a fluid for infusion via an infusion line, the syringe plunger being displaceable by a suitable drive means, for example an electric motor.

When an infusion pump is in use, particularly in medical applications, it is important that any abnormal increase in pressure in the infusion line should rapidly cause the infusion to cease. Prior art units have either incorporated means, such as a switch, linked to the mechanical drive system and responsive to an unacceptable infusion line pressure, communicated via back-pressure upon the syringe plunger, to operate an electromechanical switch to disable the drive means; or have incorporated a pressure detector in the infusion line acting to produce a signal to disable the drive means in the event of an unacceptable infusion line pressure. The disadvantages of the prior art systems are as follows:

1. in the case of the electromechanical switch coupled to the mechanical drive system, switching is usually slow owing to the need for significant mechanical travel of the system to operate the switch; and
2. in the case of the infusion line pressure sensor, for medical applications the sensor must either be sterilised or replaced for each new infusion duty, as syringes and infusion lines are most usually disposable items.

It is an object of the present invention to provide an infusion pump in which these disadvantages are at least alleviated and preferably substantially overcome.

SUMMARY OF THE INVENTION

According to a first aspect of the invention there is provided an infusion pump comprising a plunger-depression member arranged in use to depress the plunger of a syringe, drive means arranged to effect controlled axial movement of the plunger-depression member and to drive an indicating member, clutch means arranged to disengage when the back-force on the plunger-depression member exceeds a predetermined value thereby allowing the motion of the driven indicating member to cease, and motion-sensing means arranged to detect cessation of motion of the indicating means and to produce an output which disables the drive means.

The clutch means may either be in the direct line of drive from the drive means to the syringe plunger, or may be interposed between the direct line of drive and an associated motion sensing means. In the first case, disengagement of the clutch means decouples the drive means from the plunger depression member; and in the second case disengagement of the clutch means decouples the drive means from the driven indicating member.

Disabling the drive means is of course sensible in any case, even though they may be decoupled from the plunger-depression member, for safety reasons.

The motion indicating member may comprise a rotating disc, preferably a toothed or otherwise segmented disc the speed of rotation of which is indicative of the speed of movement of the plunger-depression member and thus the rate of infusion. Conveniently, the output of the motion-sensing means when the indicating member is moving is fed back to a control means, the control means being arranged to control the speed of the drive means to effect infusion at a desired rate. Thus, the output signal provided by the motion-sensing means may be compared with the expected value that would be produced if the infusion were proceeding at the desired rate and any error in the actual output signal from the motion-sensing means may be used by the control means to make appropriate adjustment to the speed of the drive means.

Adjustment means, for example an adjusting screw, may be provided by which the clutch may be arranged to disengage at different back-forces on the plunger-depression member.

The drive means may comprise a motor arranged to rotate a lead screw about an axis, the plunger-depression member being connected to a lead-screw engaging member whereby rotation of the lead-screw causes axial movement of the lead screw engaging member and thus the plunger-depression member.

In such an arrangement, the lead-screw engaging member and the plunger-depression member may be connected via an intermediate member which is constrained by guide means to move in a direction parallel to the lead screw. The guide means may comprise a guide track, guide rod, or other means for ensuring smooth motion of the intermediate member in the desired direction.

One end of the lead-screw may act as one of two disengageable faces of the clutch means. This is a convenient arrangement since, by suitably biassing the lead-screw in a direction parallel to its length, the disengagement of the clutch will be automatically effected if the back force acting on the plunger-depression member and hence on the lead-screw engaging member is sufficient to overcome the biassing force.

The infusion pump may include a visual or audible alarm which is arranged to operate on cessation of infusion. The actual mechanism by which the alarm is actuated is not of particular importance, but it may for example be actuated by a signal produced from the control means when the motion-detecting means indicates that the indicating member is no longer moving.

The invention also extends to an infusion pump as defined above in combination with a syringe and an infusion line.

The invention may be carried into practice in a number of ways, and one specific embodiment will now be described, by way of example, with reference to the accompanying drawing which is a diagrammatic view of the mechanical arrangements of a medical infusion pump incorporating in block diagram form the essential elements of a control system therefor.

DESCRIPTION OF THE PREFERRED EMBODIMENTS

Figure 1:
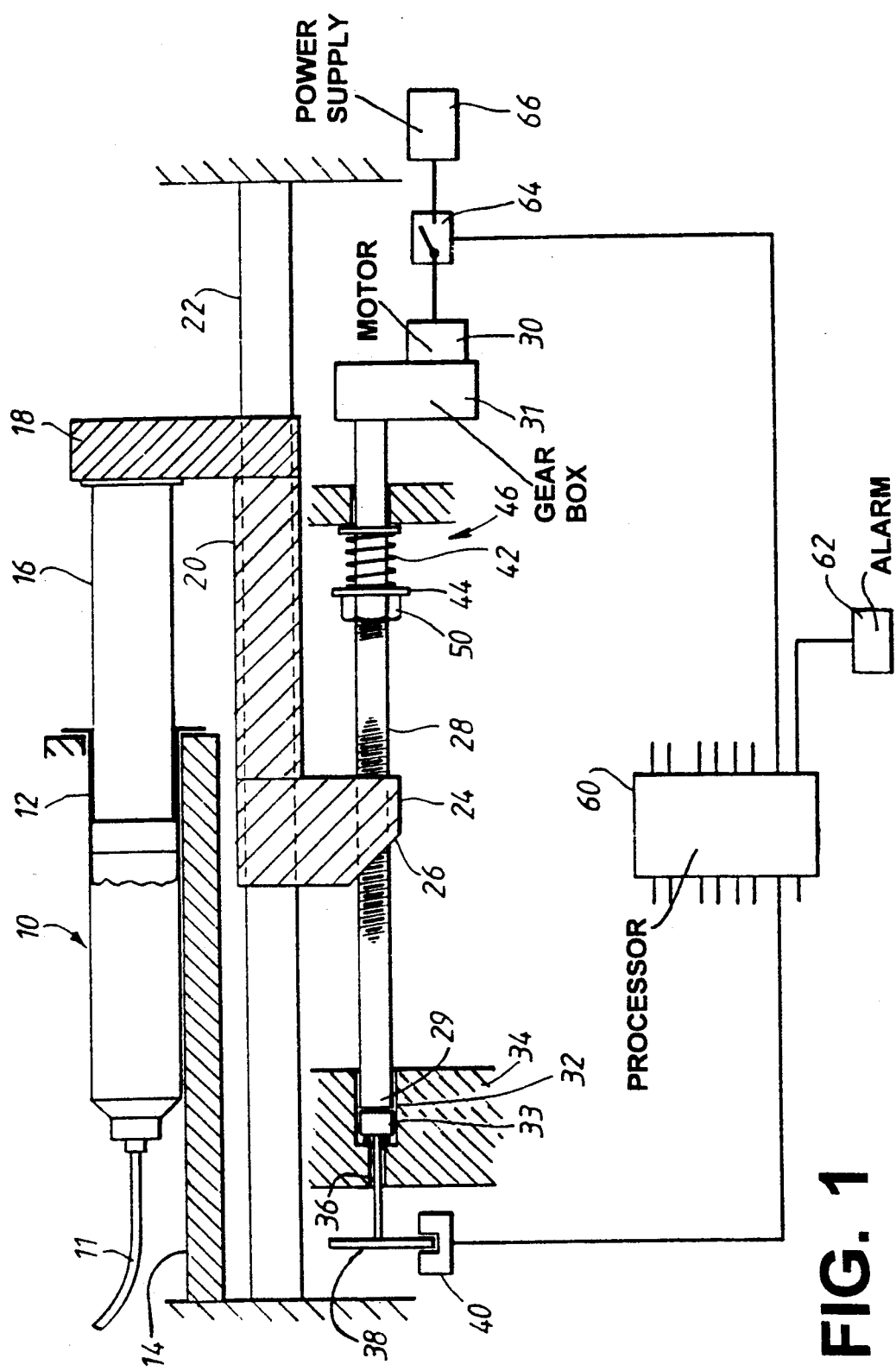
FIG. 1 shows the infusion pump operating system.

As may be seen in the drawing, a disposable syringe 10 is mounted by its barrel 12 to a support 14 a plunger 16 of the syringe 10 is engaged by a head 18 of a carriage 20, slidably mounted upon a rod 22, and arranged parallel to the axis of the syringe 10. The carriage 20 carries at is other end a tail member 24 with an internally threaded aperture 26, engaging a lead screw 28 which is also arranged parallel to the rod 22 and to the axis of the syringe 10.

The lead screw 28 is coupled at one end to an electric motor 30 and at the other to a clutch 32 mounted upon bearings in a support block 34. The clutch 32 couples the lead screw 28 to an arbor 36 which carries a segmented disc 38. A transducer 40 is mounted about the disc 38 to provide, in association with suitable processing circuitry in a processor 60, a rotary motion detection system.

The lead screw 28 also carries an assembly comprising a coil spring 42 held between washers 44 and 46. The degree of compression of the coil spring 42 can be adjusted by the setting of a nut 50 carried upon the lead screw 28.

In operation, the syringe 10 is coupled to an infusion line 11 to infuse liquid into a patient via a needle or catheter. The syringe 10 and the line 11 are disposable items. Infusion is effected by displacement of the syringe plunger 16 by the mechanical drive system comprising the motor 30, a reduction gear box 31, the lead screw 28 and the carriage 20.

With the motor 30 energised, via a power supply 66 and a controlled switch 64, the lead screw 28 rotates at a rate determined by the speed of the motor 30 and the reduction ratio of gear box 31. The motor may be programmed under the control of the processor 60 to run either continuously or for a series of predetermined intervals to infuse the liquid at a desired rate of flow.

The assembly comprising the motor 30 and the gear box 31 are supported upon the lead screw 28, but secured to prevent their rotation. Rotary motion of the lead screw 28 is translated into linear motion of the carriage 20, and hence of the syringe plunger 16, by the travel of the tail member 24 along lead screw 28.

Under normal operation conditions the end face 29 of the lead screw 28 engages a clutch plate 33 of the clutch 32 under the axial force exerted on the lead screw 28 by the coil spring 42. The infusion pressure in the line 11 is insufficient to overcome this force. In the event of a rise in pressure in the line 11, indicative of occlusion or other potentially dangerous event, a back-pressure is exerted upon the syringe plunger 16 and thus upon the carriage 20 and the tail member 24. A degree of axial force, dependent upon the magnitude of the infusion line pressure, will then be imparted to the lead screw 28 in opposition to that produced by the coil spring 42, and will tend to separate the end face 29 from the clutch plate 33.

The arbor 36 will cease to rotate when separation occurs and the rotary motion detector will cause the processor 60 to produce a signal to interrupt the power supply to the motor 30 and stop infusion. The processor 60 may also initiate a visible and/or audible alarm 62 on receipt of the motion cessation signal.

The infusion pressure at which the clutch 32 disengages is determined by the axial thrust needed to overcome the thrust exerted upon the lead screw 28 by the spring 42. The thrust exerted may be adjusted by the positioning of the nut 50, which can be calibrated to correspond to a range of infusion line pressure levels. The further to the right the nut 50 is positioned, the greater the thrust produced by the coil spring 42 and the greater the infusion pressure in the line 11 needed to terminate infusion.

In practice, with the infusion pump described, it has been found possible to effect the pre-setting of the clutch 32 by means of the nut 50 and the coil spring 42, to terminate infusion at pressures in the infusion line 11 at levels between 400 mmHg and 700 mmHg.

In an alternative arrangement (not shown), the clutch 32 may alternatively be positioned in the direct line of drive to the syringe 10 to cause direct mechanical interruption of the drive. This may be achieved by coupling the motor 30 and the gear box 31 to the arbor 36 in place of the segmented disc 38, and mounting the segmented disc 38 instead upon the other end of the lead screw 28. In this case, the axial thrust upon the lead screw 28 as a result of overpressure in the line 11 will decouple the drive from the motor 30 to the lead screw 28.

To obtain optimum performance from the infusion pump of this embodiment, the end-face 29 of the lead screw 28 and the clutch plate 33 should be plane, parallel and inelastic. In the described embodiment both are of steel.

EXAMPLE

| Overall Dimensions | 326 mm × 133 mm × 90 mm |
|---|---|
| Syringe size | 50 mls |
| Infusion line pressures: | |
| Normal | 550 mm Hg. |
| Upper limit | 700 mm Hg |
| Lower limit | 400 mm Hg |
| Lead screw pitch | 1.5 mm |
| Motor | Airpax Type No L82101-P1 Stepper Motor 5 volts 48 steps/revolution Torque 2 m Nm at 500 pulses/second |
| Gearbox Reduction ratio | 450:1 |

Typical delays between infusion line occlusion and interruption of drive: (a) Delivery rate of 100 mls/hour-20 seconds; (b) Delivery rate of 1 ml/hour-30 minutes.

(The typical delays experienced with a comparable prior art infusion pump employing mechanically-linked electromechanical switching are at least three times greater).

Infusion pumps in accordance with the invention offer a rapid and reproducible means of cutting-off infusion in the event of over-pressure in the infusion line 11 without the expense and inconvenience of infusion line pressure sensors; or the relative slowness, and difficulty of calibration and adjustment, of electromechanical switches coupled to the infusion pump drive system by mechanical linkages.

Although the specific embodiment has been described with reference to an infusion pump for medical applications, the infusion pump of the invention may be used wherever accurate repreatable volumes of liquid are to be delivered over predetermined periods, for example in the treatment of animals, in laboratory applications, and in industrial processes.

I claim:

1. An infusion pump for a syringe having a plunger comprising:
   means for holding the syringe;
   a plunger means for coupling to the plunger to depress the plunger of the syringe;
   drive means for effecting controlled movement of said plunger depression means;
   a motion indicating member;
   a clutch means operably coupled to said motion indicating member and selectively coupled to said drive means for selective movement with said drive means such that said clutch means moves said motion indicating member at a rate proportional to the rate of movement of said drive means when said clutch means is engaged with said drive means and said clutch is disengaged from said drive means when the back-force on said plunger depression means exceeds a predetermined back-force value whereby motion of said motion indicating member ceases; and means coupled to said motion indicating member for detecting motion of said motion indicating member and responsive to detecting cessation of motion of said motion indicating member for outputting an output signal which disables said drive means.

2. An infusion pump as defined in claim 1 wherein disengagement of said clutch means decouples said drive means from said plunger depression means.

3. An infusion pump as defined in claim 2, wherein said plunger depression means includes a lead screw, said drive means includes a motor, and said clutch means includes a clutch member, said motion indicating member carried on one end of said lead screw and said clutch member carried on the other end of said lead screw, said clutch member disengaging from said motor when said back force threshold is exceeded whereby said lead screw and said motion indicating member are disengaged from said motor.

4. An infusion pump as defined in claim 2 wherein said motion indicating member comprises a rotating disk.

5. An infusion pump as defined in claim 4 wherein said disk is toothed or otherwise segmented.

6. An infusion pump as defined in claim 1 wherein disengagement of said clutch means decouples said plunger depression means from said motion indicating member.

7. An infusion pump as defined in claim 6 wherein said motion indicating member includes a rotating disk.

8. An infusion pump as defined in claim 7 wherein said disk is toothed or otherwise segmented.

9. An infusion pump as defined in claim 6 further including a control means, wherein said output signal of said motion detecting means when said motion indicating member is moving is fed back to said control means, said control means for controlling the speed of said drive means to effect infusion at a desired rate.

10. An infusion pump as defined in claim 6 further including adjustment means for adjusting by which said clutch means is arranged to disengage at different back-forces on said plunger depression means.

11. An infusion pump as defined in claim 10 wherein said drive means includes a motor and said plunger depression means includes a lead screw, a lead screw engaging member, and a plunger depression member, said motor adapted to rotate said lead screw about an axis, said plunger depression member being connected to said lead screw engaging member and said lead screw engaging member operably coupled to said lead screw, whereby rotation of said lead screw causes axial movement of said lead screw engaging member and thus said plunger depression member.

12. An infusion pump as defined in claim 1 further including a control means, wherein said output signal of said motion detecting means when said motion indicating member is moving is fed back to said control means, said control means for controlling the speed of said drive means to effect infusion at a desired rate.

13. An infusion pump as defined in claim 1 further including means coupled to said motion detecting means for generating an alarm signal on cessation of motion.

14. An infusion pump as defined in claim 1 in combination with a syringe and an infusion line.

15. An infusion pump as defined in claim 1 further including adjustment means for adjusting by which said clutch means is arranged to disengage at different back-forces on said plunger depression means.

16. An infusion pump as defined in claim 15 wherein said adjustment means includes an adjustable spring bias at one end of said lead biasing said lead screw in a direction parallel to its length.

17. An infusion pump as defined in claim 15 wherein said drive means includes a motor and said plunger depression means includes a lead screw, a lead screw engaging member, and a plunger depression member, said motor adapted to rotate said lead screw about an axis, said plunger-depression member being connected to said lead screw engaging member and said lead screw engaging member operably coupled to said lead screw whereby rotation of said lead screw causes axial movement of said lead screw engaging member and thus said plunger depression member.

18. An infusion pump as defined in claim 17 wherein said lead screw engaging member and said plunger depression member are connected via an intermediate member which is constrained by guide means to move in a direction parallel to said lead screw.

19. An infusion pump as defined in claim 18 wherein said guide means includes a guide rod.

20. An infusion pump as defined in claim 19 wherein one end of said lead screw acts as one of two disengageable faces of said clutch means.

21. An infusion pump as defined in claim 20 wherein said adjustment means includes an adjustable spring bias at one end of said lead screw biassing said lead screw in a direction parallel to its length.

* * * * *

UNITED STATES PATENT AND TRADEMARK OFFICE
CERTIFICATE OF CORRECTION

PATENT NO. : 5,244,461
DATED : September 14, 1993
INVENTOR(S) : Michael L. Derlien It is certified that error appears in the above-indentified patent and that said Letters Patent is hereby corrected as shown below:

Column 3, line 34, "operation" should be --operating--;
Column 4, line 58, after "plunger" insert --depression--;
Column 5, line 2, after "clutch" insert --means--.

Signed and Sealed this

Twenty-first Day of June, 1994

Attest:

BRUCE LEHMAN

*Attesting Officer*   *Commissioner of Patents and Trademarks*